United States Patent
Didier et al.

(10) Patent No.: US 7,241,907 B2
(45) Date of Patent: Jul. 10, 2007

(54) ACETONE SOLVATE OF DIMETHOXY DOCETAXEL AND ITS PROCESS OF PREPARATION

(75) Inventors: Eric Didier, Paris (FR); Marc-Antoine Perrin, Jouy en Josas (FR)

(73) Assignee: Aventis Pharma S.A., Antony (FR)

( * ) Notice: Subject to any disclaimer, the term of this patent is extended or adjusted under 35 U.S.C. 154(b) by 449 days.

(21) Appl. No.: 10/944,254

(22) Filed: Sep. 17, 2004

(65) Prior Publication Data

US 2005/0065138 A1    Mar. 24, 2005

Related U.S. Application Data

(60) Provisional application No. 60/519,895, filed on Nov. 14, 2003.

(30) Foreign Application Priority Data

Sep. 19, 2003    (FR)    .................................. 03 11016

(51) Int. Cl.
*C07D 305/00*    (2006.01)
*C07D 407/00*    (2006.01)
*C07D 493/00*    (2006.01)

(52) U.S. Cl. ...................................................... 549/510
(58) Field of Classification Search ................. 549/510
See application file for complete search history.

(56) References Cited

FOREIGN PATENT DOCUMENTS

| EP | 0982027 | * | 3/2000 |
|----|---------|---|--------|
| WO | WO 96/30355 | * | 10/1996 |
| WO | WO 97/32869 | * | 9/1997 |

* cited by examiner

*Primary Examiner*—Margaret D. Seaman
*Assistant Examiner*—Niloofar Rahmani
(74) *Attorney, Agent, or Firm*—Balaram Gupta; Paul R. Darkes

(57) ABSTRACT

This invention discloses and claims an acetone solvate of dimethoxydocetaxel or 4-acetoxy-2α-benzoyloxy-5β,20-epoxy-1-hydroxy-7β,10β-dimethoxy-9-oxotax-11-en-13α-yl (2R,3S)-3-tert-butoxycarbonylamino-2-hydroxy-3-phenylpropionate and its preparation by crystallization from an aqueous/acetone solution.

16 Claims, 1 Drawing Sheet

ACETONE SOLVATE OF DIMETHOXY DOCETAXEL AND ITS PROCESS OF PREPARATION

This application claims the benefit of U.S. Provisional Application No. 60/519,895, filed Nov. 14, 2003 and benefit of priority of French Patent Application No. 03/11,016, filed Sep. 19, 2003, both of which are incorporated herein by reference in their entirety.

BACKGROUND OF THE INVENTION

1. Field of the Invention

The present invention relates to the acetone solvate of dimethoxydocetaxel or 4-acetoxy-2α-benzoyloxy-5β,20-epoxy-1-hydroxy-7β,10β-dimethoxy-9-oxotax-11-en-13α-yl (2R,3S)-3-tert-butoxycarbonylamino-2-hydroxy-3-phenylpropionate and to its process of preparation.

2. Description of the Art

4-Acetoxy-2α-benzoyloxy-5β,20-epoxy-1-hydroxy-7β,10β-dimethoxy-9-oxotax-11-en-13α-yl (2R,3S)-3-tert-butoxycarbonylamino-2-hydroxy-3-phenylpropionate exhibits noteworthy anticancer and antileukemic properties.

4-Acetoxy-2α-benzoyloxy-5β,20-epoxy-1-hydroxy-7β,10β-dimethoxy-9-oxotax-11-en-13α-yl (2R,3S)-3-tert-butoxycarbonylamino-2-hydroxy-3-phenylpropionate is prepared according to the process which is disclosed more particularly in international application PCT WO 96/30355 or international application PCT WO 99/25704; according to the process disclosed in these applications, the product is not crystallized and is not characterized.

All of the references described herein are incorporated herein by reference in their entirety.

SUMMARY OF THE INVENTION

It has been found that the acetone solvate of 4-acetoxy-2α-benzoyloxy-5β,20-epoxy-1-hydroxy-7β,10β-dimethoxy-9-oxotax-11-en-13α-yl (2R,3S)-3-tert-butoxycarbonylamino-2-hydroxy-3-phenylpropionate is fully characterized from a chemical viewpoint.

DETAILED DESCRIPTION OF THE INVENTION

Figure 1:
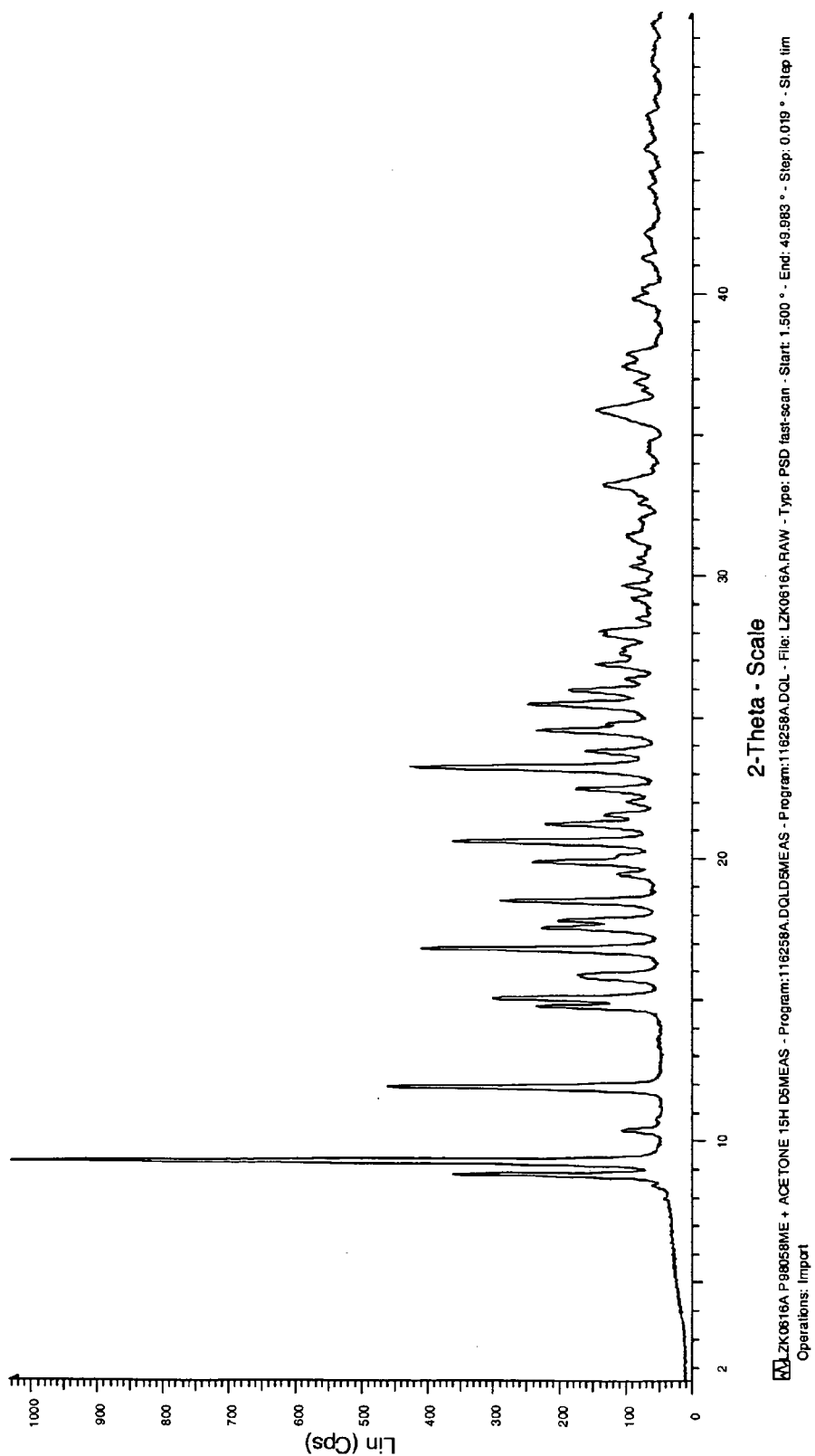
FIG. 1 is a powder x-ray diffraction (PXRD) diagram of the acetone solvate form of the product of Example 1.

According to the invention, the acetone solvate of 4-acetoxy-2α-benzoyloxy-5β,20-epoxy-1-hydroxy-7β,10β-dimethoxy-9-oxotax-11-en-13α-yl (2R,3S)-3-tert-butoxycarbonylamino-2-hydroxy-3-phenylpropionate can be obtained by crystallization of 4-acetoxy-2α-benzoyloxy-5β,20-epoxy-1-hydroxy-7β,10β-dimethoxy-9-oxotax-11-en-13α-yl (2R,3S)-3-tert-butoxycarbonylamino-2-hydroxy-3-phenylpropionate from a mixture of water and of acetone, followed by drying the isolated product under reduced pressure.

For the implementation of the process according to the invention, it can be particularly advantageous
- to dissolve 4-acetoxy-2α-benzoyloxy-5β,20-epoxy-1-hydroxy-7β,10β-dimethoxy-9-oxotax-11-en-13α-yl (2R,3S)-3-tert-butoxycarbonylamino-2-hydroxy-3-phenylpropionate in acetone,
- to treat the solution with water,
- to seed the solution with a suspension of said product in an acetone/water mixture and then to again treat with water,
- to separate the crystals obtained, then
- to dry them under reduced pressure.

Generally, 4-acetoxy-2α-benzoyloxy-5β,20-epoxy-1-hydroxy-7β,10β-dimethoxy-9-oxotax-11-en-13α-yl (2R,3S)-3-tert-butoxycarbonylamino-2-hydroxy-3-phenylpropionate is dissolved in acetone. Preferably, the amount of acetone is between 5 and 20 parts by volume (ml) with respect to the weight (in grams) of 4-acetoxy-2α-benzoyloxy-5β,20-epoxy-1-hydroxy-7β,10β-dimethoxy-9-oxotax-11-en-13α-yl (2R,3S)-3-tert-butoxycarbonylamino-2-hydroxy-3-phenylpropionate employed (ideally 10).

The preferred seeding is carried out at a concentration of 60 to 80 g (ideally 68 g) per liter of mixture comprising an acetone/water ratio by volume of from about 65/35 to about 75/25 and preferably of approximately about 68/32. The acetone/water mixture by volume at the end of precipitation is between 70/30 minimum and 30/70 maximum (ideally 45/55). The entire crystallization process takes place, according to a better way of implementing the invention, at 20±5° C. (ideally 20° C.).

The acetone solvate of 4-acetoxy-2α-benzoyloxy-5β,20-epoxy-1-hydroxy-7β,10β-dimethoxy-9-oxotax-11-en-13α-yl (2R,3S)-3-tert-butoxycarbonylamino-2-hydroxy-3-phenylpropionate which crystallizes is separated, preferably by filtration or centrifuging. Drying is carried out under a reduced pressure generally of between 0.5 and 30 kPa, preferably in the region of 0.7 kPa, at a temperature of between 30 and 60° C., preferably in the region of 40° C.

The drying of the product was studied. Thus, samples of acetone solvate of 4-acetoxy-2α-benzoyloxy-5β,20-epoxy-1-hydroxy-7β,10β-dimethoxy-9-oxotax-11-en-13α-yl (2R,3S)-3-tert-butoxycarbonylamino-2-hydroxy-3-phenylpropionate deliberately treated at a temperature above 70° C. (70 to 100° C.) shows an increasing loss in the content of acetone with the increase in the temperature. For the drying, the preferred temperature is thus between 30 and 60° C. and more preferably still is in the region of 40° C. A mean value of the content of acetone is 7%, which represents approximately the acetone stoichiometry, which is 6.5%, for a solvate comprising one molecule of acetone.

The present invention will be more fully described using the following examples, which should not be regarded as limiting the invention.

EXAMPLE 1

940 ml of purified water are added at 20±5° C. ambient temperature to a solution of 207 g of approximately 92% by weight 4-acetoxy-2α-benzoyloxy-5β,20-epoxy-1-hydroxy-7β,10β-dimethoxy-9-oxotax-11-en-13α-yl in approximately 2 liters of acetone and then seeding is carried out with a suspension of 2 g of 4-acetoxy-2α-benzoyloxy-5β,20-epoxy-1-hydroxy-7β,10β-dimethoxy-9-oxotax-11-en-13α-yl (2R,3S)-3-tert-butoxycarbonylamino-2-hydroxy-3-phenylpropionate, isolated from acetone/water, in a mixture of 20 ml of water and 20 ml of acetone. The mixture is left stirring for approximately 10 to 22 hours and 1.5 liters of purified water are added over 4 to 5 hours. The mixture is left stirring for 60 to 90 minutes and then the suspension is filtered under reduced pressure. The cake is washed on the filter with a solution prepared from 450 ml of acetone and 550 ml of purified water and is then dried in an oven at 55° C. under reduced pressure (0.7 kPa) for 4 hours. 197 g of 4-acetoxy-2α-benzoyloxy-5β,20-epoxy-1-hydroxy-7β,10β-dimethoxy-9-oxotax-11-en-13α-yl (2R,3S)-3-tert-butoxycarbonylamino-2-hydroxy-3-phenyl-propionate.acetone, comprising 0.1% of water and 7.2% of acetone (theoretically 6.5% for a stoichiometric solvate), are obtained.

Drying Study

The product is again placed in an oven and successively dried for 18 hours at 60° C. under a reduced pressure of 0.7 kPa, for 3 hours at 60° C. under a relative humidity of approximately 80% (reduced pressure of 160 mmHg) and for 18 hours at 70° C. under a relative humidity of approximately 80% (reduced pressure of 200 mmHg). At this stage, the content of water is 0.2% and the content of acetone is 4.7% (194 g). At this same stage, 1 aliquot of 1 g of the batch is dried under a reduced pressure of 5 mmHg successively for 18 hours at 80° C. (residual acetone content of 0.5%) and then for 21 hours at 100° C. (residual acetone content of 0.02%). The remainder is dried at 80° C. under a reduced pressure of 5 mmHg for 31 hours (acetone 1.7%, water 0.3%, assay with regard to such of 96.5%, purity of greater than 99%).

Operating Conditions Used for the Acquisition of the PXRD Diagram (FIG. 1)

The analyses are carried out on the Bruker D5000 diffractometer equipped with an Anton Paar TTK temperature chamber. The set-up in reflection possesses focusing geometry of Bragg-Brentano type (θ—θ). The powder is deposited on a hollow aluminum sample holder. A cobalt anticathode tube (40 kV/30 mA) supplies iron-filtered incident radiation. Radiation is emitted at two wavelengths: Co $K\alpha_1$ ($\lambda$=1.7890 Å) and Co $K\alpha_2$ ($\lambda$=1.7929 Å). Filtering by iron does not completely remove the $K\beta$ radiation ($\lambda$=1.6208 Å for cobalt), which still participates in the incident radiation at a level of 1% (manufacturer's data) of the intensity of the $K\alpha$ doublet.

Soller slits improve the parallelism of the beam. Variable front slits make it possible to retain a constant illumination area of the sample. A 1 mm collimator limits the scattering between the tube and the measuring chamber. A Braun 50 M multichannel linear detector is used. It exhibits a detection window with a width of 10° of 2θ angle. The conditions for recording the diagrams are as follows: scanning from 1.5 to 50° in 2θ, counting time of 30 seconds per degree in 2θ, under ambient conditions of temperature, pressure and relative humidity.

FIG. 1 represents the reference PXRD diagram of the solvate form comprising acetone (form A) of the product of example 1.

NMR Spectrum of the Product of Example 1

$^1$H NMR spectrum (400 MHz, CDCl$_3$, δ in ppm): 1.20 (s, 3H), 1.22 (s, 3H), 1.37 (s, 9H), 1.67 (s, 1H), 1.72 (s, 3H), 1.80 (mt, 1H), 1.88 (s, 3H), 2.17 (s, 6H), from 2.20 to 2.40 (mt, 2H), 2.36 (s, 3H), 2.70 (mt, 1H), 3.30 (s, 3H), 3.46 (s, 3H), 3.47 (mt, 1H), 3.82 (d, J=7.5 Hz, 1H), 3.86 (dd, J=11 and 6.5 Hz, 1H), 4.17 (d, J=8.5 Hz, 1H), 4.30 (d,J=8.5 Hz, 1H), 4.63 (mt, 1H), 4.80 (s, 1H), 4.97 (broad d, J=10 Hz, 1H), 5.27 (broad d, J=10 Hz, 1H), 5.44 (d, J=10 Hz, 1H), 5.64 (d, J=7.5 Hz, 1H), 6.21 (t, J=9 Hz, 1H), from 7.25 to 7.45 (mt, 5H), 7.49 (t, J=7.5 Hz, 2H), 7.60 (broad t, J=7.5 Hz, 1H), 8.09 (d, J=7.5 Hz, 2H).

What is claimed is:

1. An acetone solvate of 4-acetoxy-2α-benzoyloxy-5β,20-epoxy-1-hydroxy-7β,10β-dimethoxy-9-oxotax-11-en-13α-yl (2R,3S)-3-tert-butoxycarbonylamino-2-hydroxy-3-phenylpropionate.

2. An acetone solvate of 4-acetoxy-2α-benzoyloxy-5β,20-epoxy-1-hydroxy-7β,10β-dimethoxy-9-oxotax-11-en-13α-yl (2R,3S)-3-tert-butoxycarbonylamino-2-hydroxy-3-phenylpropionate comprising from about 5 to about 7 percent by weight of acetone.

3. A process for the preparation of the acetone solvate of 4-acetoxy-2α-benzoyloxy-5β,20-epoxy-1-hydroxy-7β,10β-dimethoxy-9-oxotax-11-en-13α-yl (2R,3S)-3-tert-butoxycarbonylamino-2-hydroxy-3-phenylpropionate, which comprises:

crystallizing 4-acetoxy-2α-benzoyloxy-5β,20-epoxy-1-hydroxy-7β,10β-dimethoxy-9-oxotax-11-en-13α-yl (2R,3S)-3-tert-butoxycarbonylamino-2-hydroxy-3-phenylpropionate from a mixture of water and acetone, which comprises seeding the solution with a suspension of said product in an acetone/water mixture and then subsequently treating with water, and which comprises drying the product obtained under reduced pressure.

4. The process as set forth in claim 3, wherein the seeding is carried out at a concentration of from about 60 to about 80 g per liter of a mixture comprising an acetone/water ratio by volume of from about 65/35 to about 75/25.

5. The process as set forth in claim 4, wherein the seeding is carried out in a mixture comprising an acetone/water ratio by volume of about 68/32.

6. The process as set forth in claim 3, wherein the acetone/water mixture by volume at the end of precipitation is from about 70/30 to about 30/70.

7. The process as set forth in claim 6, wherein the acetone/water mixture by volume at the end of precipitation is about 45/55.

8. The process as set forth in claim 3, wherein the crystallization process takes place at about 20±5° C.

9. The process as set forth in claim 4, wherein the crystallization process takes place at about 20±5° C.

10. The process as set forth in claim 5, wherein the crystallization process takes place at about 20±5° C.

11. The process as set forth in claim 6, wherein the crystallization process takes place at about 20±5° C.

12. The process as set forth in claim 7, wherein the crystallization process takes place at about 20±5° C.

13. The process as set forth in claim 3, wherein drying is carried out at a temperature in the range of from about 30 and about 60° C.

14. The process as set forth in claim 13, wherein drying is further carried out under a pressure in the region of 0.7 kPa.

15. The process as set forth in claim 3, wherein drying is carried out at a temperature of about 40° C. under a pressure in the region of 0.7 kPa.

16. The process as set forth in claim 3, wherein the preparation is carried out directly starting from the acetone solution of 4-acetoxy-2α-benzoyloxy-5β,20-epoxy-1-hydroxy-7β,10β-dimethoxy-9-oxotax-11-en-13α-yl (2R,3S)-3-tert-butoxycarbonylamino-2-hydroxy-3-phenylpropionate obtained by deprotection in an acid medium of the ester 4-acetoxy-2α-benzoyloxy-5β,20-epoxy-1-hydroxy-7β,10β-dimethoxy-9-oxotax-11-en-13α-yl (2R,4S,5R)-3-tert-butoxycarbonyl-2-(4-methoxyphenyl)-4-phenyloxazolidine-5-carboxylate.

* * * * *